US006194586B1

(12) United States Patent
Martinelli et al.

(10) Patent No.: US 6,194,586 B1
(45) Date of Patent: Feb. 27, 2001

(54) SELECTIVE SULPHONATION OF THE PRIMARY ALCOHOL OF A DIOL CONTAINING BOTH PRIMARY AND SECONDARY ALCOHOLS

(75) Inventors: Michael J. Martinelli, Zionsville; Eric D Moher, Indianapolis, both of IN (US)

(73) Assignees: Eli Lilly and Company, Indianapolis, IN (US); Wayne State University, Detroit, MI (US); University of Hawaii, Honolulu, HI (US)

( * ) Notice: Subject to any disclaimer, the term of this patent is extended or adjusted under 35 U.S.C. 154(b) by 0 days.

(21) Appl. No.: 09/029,187

(22) PCT Filed: Sep. 5, 1997

(86) PCT No.: PCT/US97/15702

§ 371 Date: Feb. 25, 1998

§ 102(e) Date: Feb. 25, 1998

(87) PCT Pub. No.: WO98/09942

PCT Pub. Date: Mar. 12, 1998

Related U.S. Application Data

(60) Provisional application No. 60/025,523, filed on Sep. 6, 1996.

(51) Int. Cl.$^7$ ............... C07C 303/02; C07D 209/34; C07D 317/02; C07D 323/02; C07D 317/00

(52) U.S. Cl. ............... 548/486; 549/336; 558/44; 558/51; 558/56; 558/61

(58) Field of Search ............... 558/61, 51, 56, 558/44; 568/868, 857; 548/486; 549/336

(56) References Cited

U.S. PATENT DOCUMENTS

| | | | | |
|---|---|---|---|---|
| 2,461,463 | * | 2/1949 | Anish | 558/51 |
| 5,126,267 | * | 6/1992 | Boaz | 558/51 X |
| 5,216,187 | * | 6/1993 | Takahashi et al. | 558/51 X |
| 5,445,963 | * | 8/1995 | Boaz | 435/280 |
| 5,550,273 | * | 8/1996 | Savu | 558/54 |

* cited by examiner

*Primary Examiner*—Floyd D. Higel
(74) *Attorney, Agent, or Firm*—John H. Engelmann; William R. Boudreaux

(57) ABSTRACT

This invention discloses an efficient process for selectively sulfonating the primary alcohol of a diol containing both primary and secondary alcohols.

11 Claims, No Drawings

SELECTIVE SULPHONATION OF THE PRIMARY ALCOHOL OF A DIOL CONTAINING BOTH PRIMARY AND SECONDARY ALCOHOLS

This application is a 371 of PCT/US97/15702 filed Sep. 5, 1997, which claims benefit of U.S. Provisional Application No. 60/025,523 filed on Sep. 6, 1996.

This invention relates to the fields of pharmaceutical and organic chemistry and provides a new catalytic process for the selective sulfonylation of a primary alcohol in the presence of a secondary or unactivated alcohol.

An efficient process for selectively sulfonating a primary alcohol in a substrate that also contains a secondary alcohol is desired for the synthesis of key intermediates to important pharmaceutical agents. Normal methods of sulfonating such a diol use a base with toluenesulfonyl chloride. As shown in Equation 1, the normal method results in a mixture of the desired primary tosylate (2), a secondary tosylate (3), and a bis-tosylate (4), as well as the starting diol (1) (eq 1).

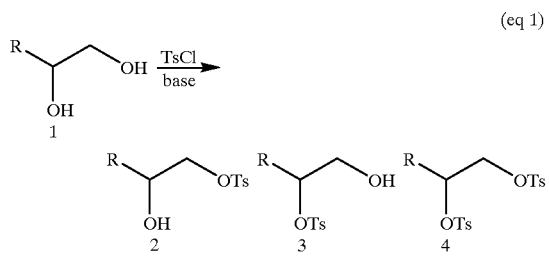

(eq 1)

The present invention provides an improved process for preparing a compound of formula I

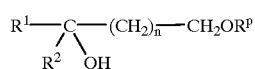

I wherein
$R^1$ is H or $R^2$; and
$R^2$ is $C_1$–$C_{12}$ alkyl; $C_2$–$C_{12}$ alkenyl, $C_3$–$C_8$-cycloalkyl, aryl, aryl-($C_1$–$C_6$ alkyl), aryl-Z—($C_1$–$C_6$ alkyl), heteroaryl, heteroaryl-($C_1$–$C_6$ alkyl), or heteroaryl-Z—($C_1$–$C_6$ alkyl), any of which may have up to three $R^5$ substituents; or
$R^1$ and $R^2$ together complete a 5-6-membered ring that may have up to three $R^5$ substituents;
$R^5$ is $C_1$–$C_{12}$ alkyl, halo, hydroxy or $C_1$–$C_3$ alkoxy;
n is 0, 1 or 2;
Z is 0 or S; and
$R^p$ is $C_1$–$C_6$ alkylsulfonyl or arylsulfonyl comprising contacting
a) a compound of formula II

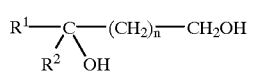

II with
b) a compound of formula $R^pSO_2X$ or $(R^pSO_2)_2O$ wherein X is halo or imidazolyl;
c) a tertiary amine; and
d) a catalytic quantity of a compound of formula $(R^a)_2Sn\,(X^a)\,m$;

wherein
$R^a$ is $C_1$–$C_{12}$ alkyl;
$X_a$ is O, Cl, Br, OAc or $OR^b$;
m is 1 or 2; and
$R^b$ is $C_1$–$C_6$ alkyl or aryl.

A preferred aspect of this invention is a process for selectively tosylating a primary alcohol in the presence of a secondary alcohol comprising reacting the primary alcohol with tosyl chloride in the presence of a catalytic quantity of Sn(IV).

The use of tin(IV) in a catalytic amount rather than in a stoichiometric amount provides important advantages. Reactions using a stoichiometric amount of tin require extensive chromatography to remove unwanted, lipophilic tin oxide. Even after such purification steps, about one to ten mole percent (1–10%) of tin contaminants remain. Such compromised product quality significantly limits the use of stannylene methodology in the preparation of pharmaceuticals.

Products produced by the process of this invention can be purified using a brief rinse and solvent removal. Additionally, the product contains dramatically less tin contaminant (less than 0.1 mole percent).

Thus, the present process provides the needed selectivity and gives a pharmaceutically acceptable intermediate that has <0.1 mole percent tin contaminant.

Preferred diol intermediates are those that are useful for preparing cryptophycin compounds.

Preferred tin catalysts are tin oxides. Particularly useful tin oxides are dibutyltin oxide and dibutyltin dimethoxide.

The present invention also provides a process for deracemizing a meso-diol comprising reacting such a diol with a chiral tin (IV) reagent.

The phrase "catalytic quantity" is understood in the art. It refers to an amount that is less than a stoichiometric amount, but is sufficient to achieve the desired results.

The term "alkyl" refers to an alkyl group with the designated number of carbon atoms. It may be saturated or unsaturated, branched or straight chain. Examples of alkyl groups include methyl, ethyl, n-propyl, iso-propyl, n-butyl, propenyl, ethenyl, sec-butyl, n-pentyl, isobutyl, tert-butyl, sec-butyl, methylated butyl groups, pentyl, tert pentyl, sec-pentyl, methylated pentyl groups and the like.

The term "alkenyl" refers to an alkyl group having from one to three double bonds. "Cycloalkyl" refers to a saturated $C_3$–$C_{12}$ cycloalkyl group.

The term, "alkoxy" means a straight or branched alkyl group bonded to an oxygen atom.

The term "aromatic group" and "heteroaromatic group" refer to common aromatic rings having 4n+2 pi electrons in a monocyclic conjugated system or a bicyclic conjugated system. The term "aryl" refers to an aromatic group. Examples of aromatic groups are phenyl, benzyl and naphthyl. Heteroaromatic groups will contain one or more oxygen, nitrogen and/or sulfur atoms in the ring. Examples of heteroaromatic groups include furyl, pyrrolyl, thienyl, pyridyl and the like. When the aromatic or heteroaromatic groups are substituted, the substituents may be attached at any available carbon atom.

The term "halo" refers to Cl, Br, F, or I.

One example of the process of this invention is shown in Equation 2

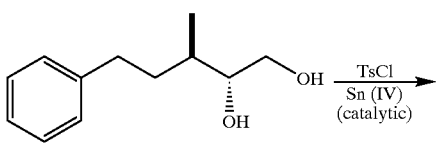

(eq 2)

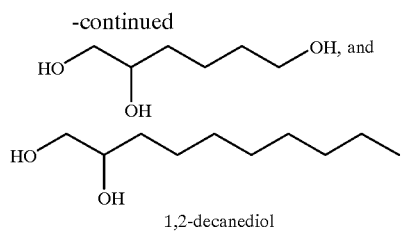

1,2-decanediol

Product 6 was tosylated selectively and cleanly under the catalytic tin conditions (<1% bis-tosylate), wherein in the absence of tin, the reaction was neither selective nor clean (>10% bis-tosylate).

Thus, tin in catalytic amounts efficiently accelerates the regioselective protection of primary alcohols. This method obviates the need for extensive chromatographic purification and provides a product with minimal tin contamination.

The process of this invention is applicable to a variety of alcohol substrates and is particularly useful for the synthesis of a key intermediate for the production of cryptophycin compounds.

Examples of formula II substrates include:

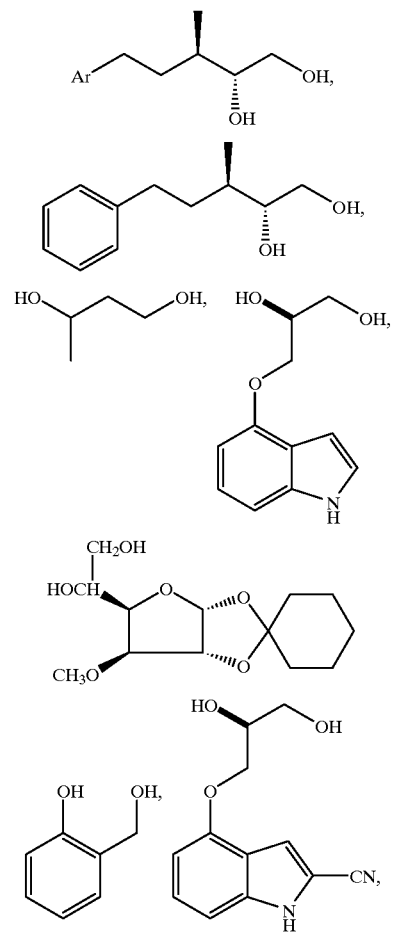

In these examples, Ar is as defined supra, and

The process of this invention is carried out in the presence of a tertiary amine. The tertiary amine can be represented by $R_3N$, wherein R can be alkyl or aryl or the $R_3$ unit together with the N represents a ring, such as pyridine or piperidine. Trialkylamines are preferred, and triethylamine is especially preferred. Diisopropylethylamine and pyridine can also be used.

The process of this invention is preferably carried out in the presence of a solvent, such as an inert organic solvent. Dichloromethane is an especially preferred solvent. Other solvents that can be used are acetonitrile, which is better than tetrahydrofuran, which is better than toluene, which is still better than methanol.

The specificity of the process of this invention is illustrated in Table 1, which compares the tosylation of diol 5 with and without tin as a catalyst:

TABLE 1

Comparison of Bis-Tosylate Formation with Tin Catalysis

| Reagent | Without Tin Catalysis | With Tin Catalysis |
| --- | --- | --- |
| diol 5 | 1.0 mole | 1.0 mole |
| TsCl | 1.0 mole | 1.0 mole |
| $Et_3N$ | 1.0 mole | 1.0 mole |
| $Bu_2Sn=O$ | 0 | 0.001 mole |
| % bis tosylate | >10% | <1% |

An especially preferred feature of the improved process is that it makes possible a shorter and more efficient synthesis of cryptophycin compounds than the known synthetic method. See Barrow, et al. J. Am. Chem. Soc. 1995, 117, 2479–2490. The process also is useful in preparing modified cryptophycin compounds of formula I

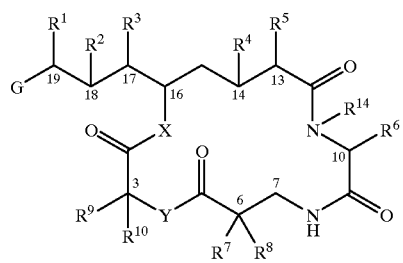

wherein

G is $C_1$–$C_{12}$ alkyl, $C_2$–$C_{12}$ alkenyl, $C_2$–$C_{12}$ alkynyl or Ar;

Ar is an aromatic or heteroaromatic group or a substituted aromatic or heteroaromatic group;

$R^1$ is halo, SR, OR, amino, mono or di-($C_1$–$C_6$-alkyl) amino, tri ($C_1$–$C_6$-alkyl) ammonium, $C_1$–$C_6$-alkylthio, di ($C_1$–$C_6$-alkyl)sulfonium, $C_1$–$C_6$-alkylsulfonyl, or $C_1$–$C_6$-alkylphosphonyl and $R^2$ is OH or SH; or $R^1$ and $R^2$ taken together form a second bond between C-18 and C-19 or together form an epoxide, aziridine, episulfide, or cyclopropyl ring;

R is H, $C_1$–$C_6$ alkyl, $C_1$–$C_6$ alkanoyl or Ar;

$R^3$ is $C_1$–$C_6$ alkyl;

$R^4$ and $R^5$ are H; or $R^4$ and $R^5$ taken together form a second bond between C-13 and C-14;

$R^7$ is H, $C_1$–$C_6$ alkyl $NR^{51}R^{52}$, -($C_1$-$C_3$-alkyl)$NR^{51}R^{52}$, or $OR^{51}$; and $R^8$ is H or $C_1$–$C_6$ alkyl; or $R^7$ and $R^8$ together form a cyclopropyl ring;

$R^{51}$ and $R^{52}$ independently are $C_1$–$C_3$ alkyl;

$R^9$ is H, $C_1$–$C_6$ alkyl, $C_2$–$C_6$ alkenyl, $C_2$–$C_6$-alkynyl or ($C_1$–$C_6$ alkyl) $C_3$–$C_5$ cycloalkyl;

$R^{10}$ is H or $C_1$–$C_6$ alkyl;

$R^{14}$ is H or a lower alkyl group;

X is O, NH or ($C_1$–$C_3$ alkyl)N—;

Y is C, O, NH, S, SO, $SO_2$ or ($C_1$–$C_3$ alkyl)N—;

$R^6$ is $C_1$–$C_6$ alkyl, substituted ($C_1$–$C_6$)alkyl, ($C_3$–$C_8$) cycloalkyl, substituted $C_3$–$C_8$ cycloalkyl, a heteroaromatic or substituted heteroaromatic group, or a group of formula IIIa, III' or III":

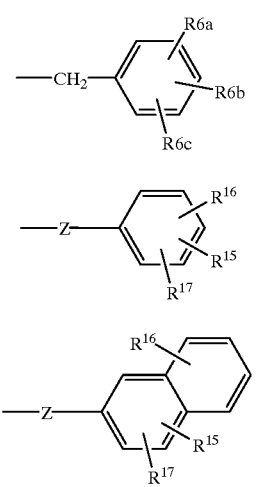

$R^{6a}$, $R^{6b}$, and $R^{6c}$ independently are H, halo or $OR^{18}$;

$R^{15}$, $R^{16}$, and $R^{17}$ independently are hydrogen, halo, ($C_1$–$C_6$)alkyl, $OR^{18}$, O-aryl, $NH_2$, $NR^{18}R^{19}$, $NO_2$, $OPO_4H_2$, ($C_1$–$C_6$ alkoxy)phenyl, Sbenzyl, $CONH_2$, $CO_2H$, $PO_3H_2$, $SO_2R^{23}$, or Z';

$R^{18}$ and $R^{19}$ independently are hydrogen or $C_1$–$C_6$ alkyl;

$R^{23}$ is hydrogen or ($C_1$–$C_3$)alkyl;

Z is —$(CH_2)_n$— or ($C_3$–$C_5$)cycloalkyl;

n is 0, 1, or 2; and

Z' is an aromatic or substituted aromatic group;

Additionally, when the process uses a tin oxide, it can be used to deracemize meso-diols using a chiral Sn=O reagent. The chiral Sn=O reagent can be prepared using chiral ligands bound in a covalent fashion or through chiral amines added to the reaction mixture which would bind to the Sn center.

Some preferred processes of this invention are those wherein:

A) the diol is of the formula:

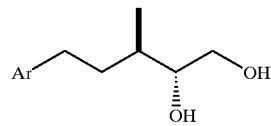

B) the tin catalyst is a tin oxide;

C) the tin catalyst is dibutyltin oxide or dibutyltin dimethoxide;

D) the process is completed in the presence of a solvent;

E) the process uses a chiral Sn(IV) reagent to provide deracemization of meso-diols;

F) the process is used to prepare an intermediate which is useful for the preparation of a cryptophycin compound; and G) the process is used to prepare an intermediate which is useful for the preparation of a cryptophycin compound of Formula I.

Appropriate starting materials and reagents used to prepare the desired substrates, and the reagents used in the processes can be selected using the guidance of the previous schemes and following examples. Most of the reagents are commercially available, and those which are not can be prepared using accepted chemical methods.

The necessary reaction time is related to the starting materials and temperature used. The optimum reaction time for a given process is, as always, a compromise which is determined by considering the competing goals of throughput, which is favored by short reaction times, and maximum yield, which is favored by long reaction times.

To further illustrate the invention the following non-limiting examples are provided.

EXAMPLE 1

Preparation of Primary Tosylate 6. (See Eq. 2)

To a 2-L 3-necked round-bottom flask, equipped with a mechanical stirrer and nitrogen inlet, was added diol 5 (58 g, 0.30 mol), $Bu_2Sn$=O (1.5 g, 0.0060 mol), $CH_2Cl_2$ (580 mL), $Et_3N$ (30.5 g, 0.30 mol) and TsCl (57.5 g, 0.30 mol). The reaction mixture was stirred at room temperature until chromatographic analysis indicated the reaction was complete (within 30–40 minutes). The reaction mixture was filtered over a pad of Hy-flo, and the filtrate was washed with water, dried over $MgSO_4$ and concentrated to yield compound 6 as a clear slightly amber oil (99%).

What is claimed is:

1. In the process for preparing a compound of formula I:

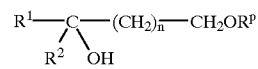

wherein $R^1$ is H; and $R^2$ is $C_1$–$C_{12}$ alkyl, $C_2$–$C_{12}$ alkenyl, $C_3$–$C_8$cycloalkyl, $C_1$–$C_{10}$ alkoxy, aryl, aryl-($C_1$–$C_6$ alkyl), aryl-Z—($C_1$–$C_6$ alkyl), heteroaryl, heteroaryl-($C_1$–$C_6$ alkyl), or heteroaryl-Z—($C_1$–$C_6$ alkyl), each of which may contain zero to three $R^5$ substituents; or $R^1$ and $R^2$ together complete a 5-6-membered ring that may have up to three $R^5$ substituents;

$R^5$ is $C_1$–$C_{12}$ alkyl, halo, hydroxy or $C_1$–$C_3$ alkoxy;

N is 0, 1, or 2;

Z is 0 or S; and $R^p$ is $C_1$–$C_7$ alkylsulfonyl or arylsulfonyl comprising reacting a) a compound of formula II $$R^1-\underset{\underset{OH}{R^2}}{\overset{}{C}}-(CH_2)_n-CH_2OR^p \qquad II$$

with b) a compound of formula $R^pSO_2X$ or $(R^pSO_3)_2O$ wherein X is halo or imidazolyl; and c) a tertiary amine, the improvement comprising adding d) a catalytic quantity of a compound of the formula $(R^a)_2Sn(X^a)_m$ wherein $R^a$ is $C_1$–$C_{12}$ alkyl;

$X^a$ is O, Cl, Br, OAc or $OR^b$;

m is 1 or 2; and $R^b$ is $C_1$–$C_6$ alkyl or aryl.

2. An improvement of claim 1 wherein n is zero.

3. An improvement of claim 1 wherein $R^2$ is aryl $(C_1$–$C_6)$ alkyl-.

4. An improvement of claim 1 wherein the $R^pSO_2$ group is tosyl.

5. An improvement of claim 1 wherein X is chloro.

6. An improvement of claim 1 wherein $X^a$ is 0.

7. An improvement of claim 1 wherein $R^a$ is $C_1$–$C_6$-alkyl.

8. A process for tosylating the primary alcohol of a diol containing both a primary alcohol and a secondary alcohol comprising reacting said diol with tosyl chloride in the presence of a catalytic quantity of tin oxide Sn(IV).

9. The process of claim 8 wherein the Sn(IV) is tin oxide.

10. The process of claim 9 wherein the tin oxide is dibutyltin oxide or dibutyltin methoxide.

11. The process of claim 8 wherein the diol is selected from the group consisting of